United States Patent
Bourqui et al.

(10) Patent No.: US 11,191,809 B2
(45) Date of Patent: Dec. 7, 2021

(54) COMPOSITION IN POWDER FORM COMPRISING IRON-MILK PROTEIN COMPLEXES AND PROBIOTIC BACTERIA

(71) Applicant: NESTEC S.A., Vevey (CH)

(72) Inventors: Bertrand Bourqui, Bern (CH); Joeska Husny, Bern (CH)

(73) Assignee: Societe des Produits Nestle S.A., Vevey (CH)

( * ) Notice: Subject to any disclaimer, the term of this patent is extended or adjusted under 35 U.S.C. 154(b) by 24 days.

(21) Appl. No.: 16/462,391

(22) PCT Filed: Dec. 14, 2017

(86) PCT No.: PCT/EP2017/082760
§ 371 (c)(1),
(2) Date: May 20, 2019

(87) PCT Pub. No.: WO2018/109063
PCT Pub. Date: Jun. 21, 2018

(65) Prior Publication Data
US 2019/0314451 A1    Oct. 17, 2019

(30) Foreign Application Priority Data
Dec. 15, 2016  (EP) .................................... 16204292

(51) Int. Cl.
*A61K 38/17* (2006.01)
*A23L 33/135* (2016.01)
(Continued)

(52) U.S. Cl.
CPC ........ *A61K 38/1709* (2013.01); *A23L 33/135* (2016.08); *A23L 33/165* (2016.08);
(Continued)

(58) Field of Classification Search
CPC ... A61K 38/1709; A61K 31/295; A23L 33/19; A23L 33/165; A23L 33/135
See application file for complete search history.

(56) References Cited

U.S. PATENT DOCUMENTS

| 6,998,143 B1 * | 2/2006 | Sher ....................... A61K 33/26 |
| | | 426/580 |
| 9,283,253 B2 * | 3/2016 | Naidu ..................... A61K 36/27 |
| 2015/0164123 A1 | 6/2015 | Mittal et al. |

FOREIGN PATENT DOCUMENTS

| CA | 2538886 | 4/2005 |
| CN | 104970099 | 10/2015 |

(Continued)

OTHER PUBLICATIONS

Merriam webster entry for "micelle" retrieved Dec. 2015 (Year: 2015).*
(Continued)

*Primary Examiner* — David W Berke-Schlessel
(74) *Attorney, Agent, or Firm* — K&L Gates LLP (57) ABSTRACT

The present invention relates to a composition in powder form comprising probiotic bacteria and at least one iron-milk protein complex. Such iron-milk protein complex advantageously does not cause significant reduction in the viability of the bacteria and thus such iron source is advantageously used to fortify a composition in powder form comprising probiotic bacteria.

13 Claims, 6 Drawing Sheets

Impact of iron source on *L. rhamnosus* survival (51) Int. Cl.
*A23L 33/165* (2016.01)
*A23L 33/00* (2016.01)
*A23P 10/40* (2016.01)
*A61K 35/747* (2015.01)
*A61K 35/745* (2015.01)
*A23L 33/19* (2016.01)

(52) U.S. Cl.
CPC ............... *A23L 33/19* (2016.08); *A23L 33/40* (2016.08); *A23P 10/40* (2016.08); *A61K 35/745* (2013.01); *A61K 35/747* (2013.01); *A23V 2002/00* (2013.01); *A23Y 2220/63* (2013.01); *A23Y 2220/73* (2013.01); *A23Y 2300/55* (2013.01)

(56) References Cited

FOREIGN PATENT DOCUMENTS

| | | |
|---|---|---|
| JP | 0753391 | 2/1995 |
| JP | 2020501526 A | 1/2020 |
| WO | 0051446 | 9/2000 |

OTHER PUBLICATIONS

Livney, Yoav D; "Milk proteins as vehicles for bioactives" Current Opinion in Colloidal & Interface Science, 15, 73-83, 2010 (Year: 2010).*
Chinju, Mathew; et al.; "A Comprehensive Review on Polymeric Micelles" International Journal of Pharmaceutical Sciences Review and Research, 61, 36-39, 2020 (Year: 2020).*
Chaneton et al. "Relationship Between Milk Lactoferrin and Etiological Agent in the Mastitic Bovine Mammary Gland" Journal of Dairy Science, 2008, vol. 91; pp. 1865-1873.
Handbook for Examination of Patents and Utility Models, Part II, Chapter 2, 56 pages.
Japan Patent Office Communication for Application No. P2019-526464, Dispatch No. 023366, dated Jan. 26, 2021, 10 pages.

* cited by examiner

COMPOSITION IN POWDER FORM COMPRISING IRON-MILK PROTEIN COMPLEXES AND PROBIOTIC BACTERIA

CROSS REFERENCE TO RELATED APPLICATIONS

The present application is a National Stage of International Application No. PCT/EP2017/082760, filed on Dec. 14, 2017, which claims priority to European Patent Application No. 16204292.3, filed on Dec. 15, 2016, the entire contents of which are being incorporated herein by reference.

FIELD OF THE INVENTION

The present invention relates to a composition in powder form comprising probiotic bacteria and at least one iron-milk protein complex. Such iron-milk protein complex advantageously does not cause significant reduction in the viability of the bacteria and thus such iron source is advantageously used to fortify a composition in powder form comprising probiotic bacteria.

BACKGROUND OF THE INVENTION

Beneficial bacteria and in particular probiotic bacteria are added to a wide range of products and namely to products in powder form to be reconstituted with a liquid, such as nutritional compositions for infant, young children, women during pregnancy, during lactation or pre-pregnancy, elderly people or people in need of specific nutrition due to an adverse medical condition. Such products usually comprise a large variety of macro- and micro-nutrients, in order to meet the nutritional needs of the consumer. For nutritional purposes, it is of paramount importance that the consumer gets appropriate amounts of the probiotic bacteria and of the other nutrients.

A particularly important micro-nutrient is iron. Worldwide, iron deficiency is one of the most prevalent nutrient deficiencies. In humans, iron is essential for the functioning of a large number of biological processes such as oxygen binding and transport, gene regulation, neurological function, immune function and regulation of cell growth and differentiation. Iron deficiency may result in anaemia, as well as a variety of health problems, such as impairment of thyroid, immune and mental functions, physical performance, cognitive development, increased sensitivity to insulin and fatigue. Iron deficiency is especially widespread in pregnant and lactating women, as well as in children.

Fortification of foods with iron is one approach to combatting iron deficiency. Therefore, the inclusion of an added iron source in dietary compositions or supplements, particularly dietary compositions or supplements for infants, small children, women pre-pregnancy, during pregnancy and/or during lactation, is highly desirable. Diverse iron compounds have been used as iron fortifying agents in food products and in nutritional supplements. For example, ferrous sulphate is widely used, owing to its relatively low price and high bioavailability.

However, the present inventors have found that a number of iron compounds, when used to fortify a composition containing a probiotic bacteria, have a deleterious effect on the viability of the probiotic bacteria (see also co-pending applications PCT/EP2016/063170 and EP16198292.1).

In most cases, the benefits of probiotic bacteria are obtained only when the bacteria are alive at the time of consumption. Thus, in order to compensate for the loss of viable probiotic bacteria and to ensure that appropriate amounts of such live bacteria are delivered to the consumer, the probiotic bacteria are usually over-dosed in the product. This solution is however not fully satisfying, because over-dosing is very costly and generates waste.

Thus, an object of the present invention is to provide compositions comprising a probiotic bacteria and an added iron source, in which the viability of the probiotic bacteria is not compromised by the presence of the added iron source.

SUMMARY OF THE INVENTION

The present inventors have surprisingly found that an iron-milk protein complex, when used as an iron source in a composition containing probiotic bacteria, do not cause a reduction in the viability of the bacteria.

In a first aspect, the invention provides a composition in powder form comprising at least one probiotic bacteria and an iron source, characterized in that the iron source is an iron-milk protein complex.

In a second aspect, the invention relates to the use of an iron source for the fortification of a composition in powder form comprising at least one probiotic bacteria, characterized in that the iron source is an iron-milk protein complex.

In a third aspect, the invention provides a process for producing a composition in powder form comprising
  a) providing a first composition in powder form;
  b) admixing to the first composition in powder form an iron source to form a second composition in powder form; and
  c) admixing at least one probiotic bacteria to the first composition in powder form before or at the same time as the iron source or admixing at least one probiotic bacteria to the second composition in powder form, after the addition of the iron source,
characterized in that the iron source is an iron-milk protein complex.

In a fourth aspect, the invention provides a method for producing a product comprising reconstituting in a liquid a composition in powder form comprising at least one probiotic bacteria and an iron source, characterized in that the iron source is an iron-milk protein complex.

In a fifth aspect, the invention provides a product obtainable or obtained by the method of the invention.

In a sixth aspect, the invention provides a method for providing a nutrition to an individual comprising feeding the individual with a product of the invention, which is an edible product.

In a seventh aspect, the invention provides an edible composition in powder form comprising at least one probiotic bacteria and an iron source, for use in the prevention, reduction and/or treatment of iron deficiency in an individual, characterized in that the iron source is an iron-milk protein complex.

In an eighth aspect, the invention provides a method for reducing and/or preventing the loss of probiotic bacteria during reconstitution of a composition in powder form comprising at least one probiotic bacteria and an added iron source, characterized in that an iron-milk protein complex is used as the added iron source.

DETAILED DESCRIPTION OF THE INVENTION

Definitions

As used herein, the terms "iron-milk protein complex" designate a complex formed of iron cations chelated with milk proteins. Milk proteins are intended to encompass casein, whey proteins and mixtures thereof, as well as derivatives or fractions of casein or whey protein.

As used herein, the term "probiotic bacteria" refers to live bacterial cell preparations with a beneficial effect on the health or well-being of the host [Salminen S, et al., "Probiotics: how they should be defined", Trends Food Sci. Technol, (1999), 10, 107-10].

Bacteria are considered as "live" when they are able to multiply under controlled culture conditions and form colonies or suspensions or when the microorganism metabolic activity and/or membrane integrity can be established using methods known to the person skilled in the art, such as for example flow cytometry. Dried probiotic bacteria are considered as live when they are able to multiply and/or when membrane integrity can be established, as described above, after reconstitution of the bacteria with a liquid, such as an aqueous liquid, preferably water.

For the purpose of the present invention, "reconstitution" refers to dissolution or suspension of a powder in a liquid such as an aqueous liquid, preferably water, a specific reconstitution medium as used in analytical microbiology, or a drink like milk or juice. The liquid used for reconstitution may be cold or warm. Preferably it refers to reconstitution with an aqueous liquid, preferably with water.

An "aqueous liquid" is intended for the purpose of the present invention as a liquid comprising at least one aqueous phase. It can be for example an emulsion, an aqueous solution or dispersion or water. Preferably it is an oil-in-water emulsion, an aqueous solution or suspension or water. More preferably it is an aqueous solution or suspension or water. Most preferably it is water.

The term "iron" is herein intended as designating either $Fe^{2+}$ or $Fe^{3+}$, depending on the iron source used, unless otherwise specified.

An "added iron source" is intended for the purpose of the present invention as a ferrous or ferric compound added to the composition for the sole benefit of iron supplementation. Depending on its nature, the composition may comprise iron coming from other ingredients, for example from milk, fruit, vegetable, cereal or fibre components. Iron present in such ingredients is not intended here as an "added iron source", because it is inherently present in an ingredient that is not primarily added for its iron content, but for its overall nutritional value.

An iron source is intended for the purpose of the present invention as being "substantially the only added iron source" in the composition, provided that other added iron sources are used in a sufficiently small amount not to cause a statistically significant loss of viable probiotic bacteria. The skilled person can assess whether a statistically significant loss of viable bacteria is caused by applying the method described in the examples of the present application and applying commonly known statistical techniques for the analysis of the results.

The term "exogenous", when referring to iron or phosphorus in the complex refers to iron and/or phosphorus that has been added during the process of production of the complex and thus it refers to iron or phosphorus that was not natively chelated with the milk proteins.

The term "nutritional composition" designates a product intended to provide a complete nutrition or a supplemental nutrition to an individual (i.e. to fulfil essential nutritional needs of such individual) and in which the prominent objective is to provide nutrition. A nutritional composition aims at providing specific nutrients to an individual having special nutritional needs, such as infants, young children, pregnant or lactating women, elderly people or people with adverse medical condition requiring special food (e.g. tube feeding compositions or compositions for paediatric subjects). Products in which the hedonic aspect is prominent and nutritional qualities are not of primary importance are excluded from the "nutritional products". Nutritional compositions preferably comprise proteins, fats, carbohydrates and diverse micro-nutrients.

In the present invention, the term "infant" means a child between birth and 12 months of age. The terms "young child" refer to a child between 12 months and 5 years of age, preferably between 12 months and 3 years of age.

The expression "infant formula" as used herein refers to a foodstuff intended for particular nutritional use by infants and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The infant formulas can encompass the starter infant formulas and the follow-up or follow-on formulas. Generally a starter formula is for infants from birth as breast-milk substitute. A follow-up or follow-on formula is given from the 6th month onwards. It constitutes the principal liquid element in the progressively diversified diet of this category of person. It is to be understood that infants can be fed solely with infant formulas, or that the infant formula can be used as a supplement or complement of human milk.

The "growing-up milks" (or GUMs) are given from one year onwards. It is generally a milk-based beverage adapted for the specific nutritional needs of young children.

The expression "baby food" means a foodstuff intended for particular nutritional use by infants or children such as young children, during the first years of life.

The expression "infant cereal composition" means a cereal-based foodstuff intended for particular nutritional use by infants or children such as young children, during the first years of life.

The term "fortifier" refers to nutritional compositions suitable for mixing with breast milk or infant formula. The "breast milk" should be understood as the mother's milk or the colostrum of the mother or a donor's milk or the colostrum of a donor's milk.

The term "supplement" refers to a composition that can be used to supplement, or complement, the nutrition of an individual.

The term "prebiotic" means non-digestible carbohydrates that beneficially affect the host by selectively stimulating the growth and/or the activity of healthy bacteria in the colon of humans (Gibson G R, Roberfroid M B. Dietary modulation of the human colonic microbiota: introducing the concept of prebiotics. J Nutr. 1995; 125:1401-12).

Composition

The composition of the present invention is a composition in powder form comprising at least one probiotic bacteria and an iron source, said iron source being an iron-milk protein complex.

The present inventors have surprisingly found that, within the many constituents of a complete nutritional composition, such as an infant formula, added iron was responsible for significant loss of probiotic bacteria in the reconstituted composition. Also, the present inventors have identified that iron-milk protein complexes could advantageously be used as nutritional sources of iron, in combination with probiotic bacteria, without causing significant loss of viability of such probiotic bacteria.

The milk protein may be casein, a derivative or a fraction of casein, whey, a derivative or fraction of whey or a mixture thereof. Preferably, the protein is a phosphoprotein. In a preferred embodiment the milk protein in the iron-milk protein complex comprises casein and/or a derivate or fraction of casein. Most preferably, the milk protein in the complex comprises casein. In a preferred embodiment the milk protein present in the complex consists of casein and/or derivatives or fractions of casein. More preferably the milk proteins in the complex consists of casein.

Casein can be obtained from diverse sources like milk, sodium caseinate, potassium caseinate, ammonium caseinate, rennet caseinate, acid casein, such as lactic casein and/or non-fat milk solids. Preferably, it is sodium caseinate, potassium caseinate, ammonium caseinate and/or lactic casein.

In a preferred embodiment, the complex is a non-micellar complex.

In an embodiment, the milk protein is derived from a milk source having a ratio of protein to calcium that is of at least 45:1. Preferably the protein/calcium w/w ratio in the milk source is of at least 58:1, more preferably it is of 58:1 to 640:1, most preferably it is of 70:1 to 95:1. This represents a significant decrease of the amount of calcium in the milk source, as cow milk normally has a protein/calcium w/w ratio of 26:1. In another preferred embodiment, the milk protein is derived from a milk source wherein at least 70% w/v of the calcium has been removed from the milk source. Such milk source is preferably selected from whole milk, skimmed milk, low lactose milk, ultrafiltration retentate, concentrated milk and combinations thereof. In an embodiment the milk is bovine milk. Removal of calcium from the milk source is advantageous in that it helps in the binding of higher amounts of iron to the milk proteins, namely by removing the chelated calcium, which can be replaced by iron.

In another embodiment, the iron-milk protein complex comprises exogenous phosphorus, more preferably exogenous orthophosphorus. Preferably, the protein to phosphorus (preferably to orthophosphorus) w/w ratio is form 64:1 to 6.25:1, preferably less than 32:1 to 6.25:1, preferably from less than 32:1 to 8:1, more preferably from 28:1 to 8:1, even more preferably from 25:1 to 8:1, most preferably from 20:1 to 8:1. The presence of phosphorus is advantageous in that it helps in the effective binding of iron to the milk proteins, thus contributing to the binding or high amounts of iron in the complexes.

In another preferred embodiment, the complex is soluble in a solution at physiological pH, preferably between pH 6.6 and 6.9. Such solubility is beneficial to avoid formation of insoluble precipitates in liquid solution at such pH and also contributes to the good bioavailability to the complex.

Preferably, the iron in the complex is exogenous iron. It is advantageous that the complex comprises exogenously added iron, because only little amounts of iron are naturally bound to milk proteins, such as casein. Preferably the complex comprises more than 1% w/w of bound iron, more preferably from 1 to 20% w/w of bound iron, even more preferably, 1 to 8% w/w, most preferably from 4 to 8% w/w of bound iron. More preferably the w/w ratio of protein to iron (preferably to exogenous iron) is between 92:1 and 19.5:1, preferably between 90:1 and 19.5:1, more preferably between 80:1 and 19.5:1, most preferably between 50:1 and 19.5:1. It is particularly advantageous to be able to have such high amounts of iron bound to the milk proteins in the complex because the higher the iron load in the complex, the smaller the amount of complexes needed to fortify a product.

In a preferred embodiment the iron cation in the complex is $Fe^{3+}$.

In a preferred embodiment the complex is provided in the form of a powder.

Particularly preferred complexes are those described in US 2015/0164123 and in WO00/51446, which are both hereby incorporated as reference. Such documents provide detailed description of processes that can be used to produce complexes such as those described above and particular embodiments of complexes that can advantageously be used for the purpose of the present invention.

Most preferred are the complexes described in US 2015/0164123. They are particularly advantageous in that they are soluble in aqueous liquid food products or beverages even when high amounts of iron are bound to the milk protein in the complexes. The complexes thus advantageously do not form insoluble precipitates, which would generate haze when added to transparent beverages and solutions and which may provide undesirable sandy texture to food products and beverages. Further advantages of the above-described complexes can be found in the cited reference document US 2015/0164123.

Now, the present inventors have found that most iron sources, such as the widely used ferrous sulphate heptahydrate and dissolved ferrous sulphate in spray-dried form, both cause significant loss of viability of probiotic bacteria, whereas no significant loss of viability of probiotic bacteria is observed with iron-milk protein complexes such as described herein. Without wishing to be bound by theory, the present inventors have identified that probiotic bacteria were particularly sensitive to free iron at the time of reconstituting the powdered composition with a liquid. At the time of reconstitution of the powdered composition with a liquid, slow liberation of free iron is believed to let sufficient time for the probiotic bacteria to re-hydrate before it is faced with free iron, thus reducing the viability loss of the probiotic bacteria.

This positive effect is observed when the iron-milk protein complex is used as such and as well when such complexes are dispersed in an amorphous matrix, provided that the complexed structure remains. Such ingredient with complexes dispersed in a matrix can be obtained by mixing the complexes in a carrier solution and spray-drying the carrier solution. Suitable carrier comprise for example maltodextrin. The person skilled in the art can routinely assess if a product or ingredient comprises iron-milk protein complexes by combining a protein identification assessment such as SDS-PAGE, mineral analysis using ICP atomic emission spectroscopy as well as by doing a "free iron" test with a compound such as potassium hexacyanoferrate that involves colour changes in the presence of $Fe^{2+}$ and $Fe^{3+}$.

The use of the above-described iron-milk protein complexes is particularly advantageous, in that they are characterized at the same time by good bioavailability and by low detrimental impact on probiotic bacteria viability. It has been shown that iron-milk proteins such as described above are characterized by a bioavailability similar to that of ferrous sulphate, which is the golden standard in terms of bioavailability in human. See for example in US 2015/0164123 and WO 00/51446.

In a preferred embodiment, at least 50 wt %, more preferably at least 60 wt %, more preferably at least 70 wt %, more preferably at least 80 wt %, even more preferably at least 90 wt % of the added iron is in the form of an iron-milk protein complex as defined above. Even more preferably, the iron-milk protein complex as defined above is substantially the only added iron source in the composition. Most preferably, the iron-milk protein complex as defined above is the only added iron source in the composition.

The added iron source is preferably present in an amount such as to provide from 1 to 300 mg, preferably 1 to 250 mg, more preferably 1 to 200 mg, more preferably 1 to 100 mg, even more preferably 1 to 75 mg, most preferably 1 to 50 mg of iron per 100 g of composition, based on the total dry weight of the composition.

Any live probiotic bacteria can be used in the composition of the invention. The examples provided in the present application show that the above-described complexes do not impair the viability of probiotic bacteria. The effect is not strain-specific and can be applied to a wide range of bacterial strains.

Examples of probiotic bacteria that can be present in the composition of the present invention include bifidobacteria, lactobacilli, lactococci, enterococci, streptococci, *Leuconostoc*, *Escherichia*, propionibacteria, or combinations thereof, preferably it is a bacteria of the *Lactobacillus* or of the *Bifidobacterium* genus.

Preferably the probiotic bacteria is selected among the species *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus rhamnosus, Lactobacillus johnsonii, Lactobacillus plantarum, Lactobacillus fermentum, Lactobacillus reuteri, Lactococcus lactis, Streptococcus thermophilus, Lactococcus diacetylactis, Lactococcus cremoris, Lactobacillus delbrueckii* subsp. *bulgaricus, Lactobacillus delbrueckii* subsp. *lactis, Lactobacillus helveticus, Escherichia coli, Enterococcus faecium, Leuconostoc pseudomesenteroides, Bifidobacterium bifidum, Lactobacillus gasseri, Lactobacillus sakei, Streptococcus salivarius*, as well as any of their subspecies and/or mixtures thereof.

More preferably, it is selected from the species *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus rhamnosus, Lactobacillus johnsonii, Lactobacillus plantarum, Lactobacillus fermentum, Lactobacillus reuteri, Lactobacillus delbrueckii* subsp. *bulgaricus, Lactobacillus delbrueckii* subsp. *lactis, Lactobacillus helveticus, Bifidobacterium bifidum, Lactobacillus gasseri, Lactobacillus sakei* and mixtures thereof.

Examples of bacterial strains that can advantageously be present in the composition include *Bifidobacterium longum* (deposited as ATCC BAA-999), *Bifidobacterium longum* (deposited as CNCM I-2618), *Bifidobacterium breve* (deposited as CNCM I-3865), *Bifidobacterium lactis* (deposited as CNCM I-3446), *Lactobacillus johnsonii* (deposited as CNCM I-1225), *Lactobacillus paracasei* (deposited as CNCM I-2116), *Lactobacillus rhamnosus* (deposited as CGMCC 1.3724), *Streptococcus thermophilus* (deposited as CNCM I-1422), *Streptococcus thermophilus* (deposited as CNCM I-4153), *Streptococcus thermophilus* (deposited as CNCM I-1985), *Streptococcus thermophilus* (deposited as CNCM I-3915), *Lactobacillus casei* (deposited as CNCM I-1518), *Lactobacillus casei* (deposited as ACA-DC 6002), *Escherichia coli* Nissle (deposited as DSM 6601), *Lactobacillus bulgaricus* (deposited as CNCM I-1198), *Lactococcus lactis* (deposited as CNCM I-4154), or combinations thereof.

More preferred bacterial strains include *Bifidobacterium longum* (deposited as ATCC BAA-999), *Bifidobacterium longum* (deposited as CNCM I-2618), *Bifidobacterium breve* (deposited as CNCM I-3865), *Bifidobacterium lactis* (deposited as CNCM I-3446), *Lactobacillus johnsonii* (deposited as CNCM I-1225), *Lactobacillus paracasei* (deposited as CNCM I-2116), *Lactobacillus rhamnosus* (deposited as CGMCC 1.3724), *Lactobacillus casei* (deposited as CNCM I-1518), *Lactobacillus casei* (deposited as ACA-DC 6002), *Streptococcus thermophilus* (deposited as CNCM I-3915) and *Lactobacillus bulgaricus* deposited as (CNCM I-1198) or combinations thereof.

In a further preferred embodiment the probiotic bacteria is selected from *Bifidobacterium longum* (deposited as ATCC BAA-999), *Lactobacillus rhamnosus* (deposited as CGMCC 1.3724) and *Lactobacillus paracasei* (deposited as CNCM I-2116) and mixtures thereof.

The probiotic bacteria is preferably present in the composition in an amount of at least 5E+06 CFU per gram of composition, on a dry weight basis, preferably 5E+06 to 1E+12 CFU per gram of composition, more preferably 5E+06 to 5E+11 CFU per gram of composition, most preferably 5E+06 to 5E+10 CFU per gram of composition.

The selected probiotic bacteria may be cultured according to any suitable method and prepared for addition to the composition by known techniques such as freeze-drying or spray-drying for example. Alternatively, bacterial preparations can be bought from specialist suppliers such as DSM, Dupont Danisco, Morinaga, Institut Rosell, Christian Hansen and Valio, already prepared in a suitable form for addition to a composition in powder form.

The composition in powder from may be in the form of free powder or in the form of compressed powder, such as in the form of a tablet. Preferably the composition in powder form is not intended to be used in the form of a powder, but is to be reconstituted in a liquid, preferably in an aqueous liquid, most preferably in water, before use.

Preferred compositions in powder form of the invention include a food or beverage product, an animal feed product, a nutritional supplement for human or animal, a pharmaceutical composition or a cosmetic composition.

In another preferred embodiment, the composition in powder form is an edible composition.

Food and beverage products include all products intended to be consumed orally by human beings, for the purpose of providing nutrition and/or pleasure. In a preferred embodiment, the product is a nutritional composition. More preferably it is a nutritional composition selected from an infant formula, a growing-up milk, a baby food, an infant cereal composition, a fortifier, a supplement and a nutritional composition for pregnant or lactating women. More preferably, it is selected from an infant formula, a growing-up milk, an infant cereal composition and a nutritional composition for pregnant or lactating women. Even more preferably, it is selected from an infant formula, a growing-up milk and an infant cereal composition. Most preferably, it is an infant formula or a growing-up milk.

The product can also be in the form of an animal feed product or a nutritional supplement for animals. Preferably, the animal is a mammal. Examples of animals include primates, cows, sheep, goats, horses, dogs, cats, rabbits, rats, mice, fish, birds and the like.

Nutritional supplements in powder form include free powder or compressed powder supplements, and typically encompass supplements to be dissolved in water or to be sprinkled on wet food or in a beverage. Such supplements are intended to provide additional nutrients and/or a health benefit to the subject consuming it, as well as other beneficial ingredients, including probiotic bacteria and iron. A supplement according to the present invention can be used for providing nutrients and/or a health benefit to human beings, as well as to animals, as defined above. Nutritional supplements include for example powder supplements to be added to breast milk, for example for premature or low birth weight infants. It also includes supplements for women pre-pregnancy, during pregnancy and/or during lactation.

Pharmaceutical compositions are compositions intended to treat or to prevent an adverse medical condition in a subject in need thereof.

Cosmetic compositions are typically intended for an aesthetic effect on the body and may preferably be administered by oral route.

The composition, preferably the nutritional composition, preferably comprises protein, carbohydrates, fats, vitamins and/or other minerals. Preferably, it comprises all of these types of nutrients.

The proteins may be intact or hydrolysed (extensively or partially hydrolysed).

The nutritional composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well as small amounts of long chain polyunsaturated fatty acids (LC-PUFAs), such as arachidonic acid (ARA), docosahexaenoic acid (DHA) and/or eicosapentaenoic acid (EPA). Such LC-PUFAs may be provided in the form of fish oil or microbial oil. Iron-milk protein complexes such as herein described advantageously cause little or even no oxidation of LC-PUFAs.

The composition according to the present invention may contain a carbohydrate source, such as lactose, maltodextrin, starch and mixtures thereof. The composition according to the present invention may also contain a particular type of carbohydrates: prebiotics. The prebiotics that may be used in accordance with the present invention are not particularly limited and include all food substances that promote the growth of probiotics or health beneficial micro-organisms in the intestines. Preferably, they may be selected from the group consisting of oligosaccharides, optionally containing fructose, galactose, and mannose; dietary fibers, in particular soluble fibers, soy fibers; inulin; or mixtures thereof. Some examples of prebiotics are fructo-oligosaccharides (FOS), galacto-oligosaccharides (GOS), isomalto-oligosaccharides (IMO), xylo-oligosaccharides (XOS), arabino-xylo oligosaccharides (AXOS), mannan-oligosaccharides (MOS), inulin, polydextrose, glycosylsucrose (GS), lactosucrose (LS), lactulose (LA), palatinose-oligosaccharides (PAO), malto-oligosaccharides, gums and/or hydrolysates thereof, pectins and/or hydrolysates thereof. In a particular embodiment, the prebiotics may be fructooligosaccharides and/or inulin. Suitable commercial products that can be used include combinations of FOS with inulin such as the product sold by BENEO under the trademark Orafti, or polydextrose sold by Tate & Lyle under the trademark STA-LITE®.

The prebiotics can also be a BMO (bovine's milk oligosaccharide) and/or a HMO (human milk oligosaccharide) such as N-acetylated oligosaccharides, sialylated oligosaccharides, fucosylated oligosaccharides and any mixtures thereof.

A particular example of prebiotic is a mixture of galacto-oligosaccharide(s), N-acetylated oligosaccharide(s) and sialylated oligosaccharide(s) in which the N-acetylated oligosaccharide(s) represent 0.5 to 4.0 wt % of the oligosaccharide mixture, the galacto-oligosaccharide(s) represent 92.0 to 98.5 wt % of the oligosaccharide mixture and the sialylated oligosaccharide(s) represent 1.0 to 4.0 wt % of the oligosaccharide mixture. For example a composition for use according to the invention can contain from 2.5 to 15.0 wt % CMOS-GOS on a dry matter basis with the proviso that the composition comprises at least 0.02 wt % of an N-acetylated oligosaccharide, at least 2.0 wt % of a galacto-oligosaccharide and at least 0.04 wt % of a sialylated oligosaccharide. WO2006087391 and WO2012160080 provide some examples of production of such an oligosaccharide mixture.

The composition of the invention may also contain all vitamins, minerals and other micronutrients, understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended target group.

Iron-milk protein complexes such as herein described advantageously cause little or even no oxidation of vitamins, such as vitamin A and vitamin C. Also the iron-milk protein complexes such as described herein cause little or even no oxidation of polyphenols, thus it is also preferred the composition of the present invention comprises polyphenols.

Process for Producing a Composition in Powder Form

In an embodiment, the present invention relates to a process for producing a composition in powder form comprising
  a) providing a first composition in powder form;
  b) admixing an iron source with the first composition in powder form to obtain a second composition in powder form; and
  c) admixing at least one probiotic bacteria to the first composition in powder form before or at the same time as the iron source or admixing at least one probiotic bacteria to the second composition in powder form, after the addition of the iron source,
characterized in that the iron source is an iron-milk protein complex.

The composition in powder form, the iron source and the probiotic bacteria are as defined in any of the embodiments described above in the "composition" section.

The first composition in powder form can be prepared using any method known in the art, such as for example spray-drying. In such a method, the ingredients of the composition are mixed in a wet mix and sprayed in a drying tower to form a powder. Sensitive ingredients, like minerals or vitamins for example, may also be added in dry form before, at the same time or after addition of the iron source and/or of the probiotic bacteria. For example, it is common that the iron source is added to the first composition in powder form as a trace element premix comprising diverse minerals and vitamins.

The probiotic bacteria is preferably added in the form of a pre-blend comprising a carrier and optionally protective agents. Carriers for probiotic bacteria are well-known to the person skilled in the art of incorporating probiotic bacteria into products. The carrier is preferably a carbohydrate, such as for example maltodextrin. A wide variety of protective agents are known to the person skilled in the art. Particularly suitable protective agents are those described in the co-pending patent application PCT/EP16/065359 of the same applicant.

The steps of admixing the probiotic bacteria and the step of admixing the iron source may be performed using any method known in the art for mixing such types of ingredients with a powder composition. For example the admixture can be performed by dry-mixing, by direct addition in the spray-drying tower, in a fluid bed, coater or agglomerator or at final stage of extrusion or roller drying. Preferably, the probiotic bacteria and/or the iron source are admixed with the composition in powder form by dry-mixing or by addition in a fluid bed. Most preferably, the probiotic bacteria and/or the iron source are admixed with the composition in powder form by dry-mixing.

In a preferred embodiment, at least 50 wt %, more preferably at least 60 wt %, more preferably at least 70 wt %, more preferably at least 80 wt %, even more preferably at least 90 wt % of the added iron in the composition is in the form of an iron source as defined above. Even more preferably, the iron source as defined above is substantially the only added iron source in the composition. Most preferably, the iron source as defined above is the only added iron source in the composition.

Use of Iron-Milk Protein Complexes for the Fortification of a Composition in Powder Form Ion-milk protein complexes can advantageously be used for the fortification of a composition in powder form comprising at least one probiotic bacteria. Such iron sources advantageously provide bioavailable iron, while causing no significant loss of viability of probiotic bacteria during reconstitution of the powder with a liquid, such as water.

Iron-milk protein complexes having a bioavailability similar to that of ferrous sulphate, as described above, they are particularly useful to fortify food products.

In another embodiment, the present invention relates to a method for fortifying a composition in powder form comprising at least one probiotic bacteria, said method comprising the steps of
  a) providing a first composition in powder form;
  b) admixing to the first composition in powder form an iron source to produce a second composition in powder form; and
  c) admixing at least one probiotic bacteria to the first composition in powder form before or at the same time as the iron source or admixing at least one probiotic bacteria to the second composition in powder form, after the addition of the iron source,
wherein the iron source is an iron-milk protein complex.

The first composition in powder form, the second composition in powder form and the process steps are as defined in the section above related to the process for producing the composition of the invention. Also, the composition in powder form, the iron source and the probiotic bacteria are as described above in any embodiment of the "composition" section.

In a preferred embodiment, at least 50 wt %, more preferably at least 60 wt %, more preferably at least 70 wt %, more preferably at least 80 wt %, even more preferably at least 90 wt % of the added iron in the composition is in the form of an iron source as defined above. Even more preferably, the iron source as defined above is substantially the only added iron source in the composition. Most preferably, the iron source as defined above is the only added iron source in the composition.

A Composition for Use in a Method to Prevent, Reduce and/or Treat Iron Deficiency The composition of the invention being fortified with a highly bioavailable iron source, as described above, the present invention also relates to a composition for use in a method to prevent, reduce and/or treat iron deficiency in an individual.

Method for Producing a Product

The invention relates to a method for producing a product, preferably an edible product, comprising reconstituting in a liquid a composition in powder form comprising at least one probiotic bacteria and an iron source, characterized in that the iron source is an iron-milk protein complex.

The composition in powder form, the probiotic bacteria and the iron source are as defined in any of the embodiments described above.

The use of an iron-milk protein complex is particularly advantageous when the composition in powder form is reconstituted in a liquid. The present inventors have found that probiotic bacteria were particularly sensitive at the time of rehydration and that loss of viability was particularly acute when the composition in powder form was reconstituted with a liquid such as water. The present inventors have also discovered that iron-milk protein complexes did not cause significant loss of viability of probiotic bacteria at that critical moment, contrary to common sources of iron, such as ferrous sulphate heptahydrate or dissolved ferrous sulphate in spray-dried form.

Reconstitution is preferably carried out with an aqueous liquid, most preferably water. The amount of liquid, preferably water, added for the reconstitution depends on the type of product that is prepared. What is key for the purpose of the present invention is that enough liquid is added to reconstitute the probiotic bacteria to its natural moisture content.

Product

The invention also relates to a product, preferably an edible product, obtainable or obtained by the method described above. The product comprises the composition in powder form, as defined in any embodiment of the present invention, reconstituted in a liquid. Preferably, it is reconstituted in an aqueous liquid, preferably in water.

Preferably, the product is a nutritional product, obtained by reconstitution of a nutritional composition as described above.

Method for Providing a Nutrition

A method for providing a nutrition to an individual comprising feeding the individual with an edible product of the invention, preferably with a nutritional product of the invention, is also contemplated. The product used in this method is a food or beverage composition. Preferably, it is a nutritional composition as defined above. Such products are particularly advantageous because they comprise a bioavailable source of iron and stable concentrations of probiotic bacteria, as no significant loss of probiotic bacteria is caused by the added iron source.

In an embodiment the method comprises the steps of
a) reconstituting an edible composition in powder form according to any of the embodiments of the invention; and
b) feeding an individual with the reconstituted composition.

In an embodiment, the individual is an individual having an iron deprivation or an individual at risk of developing an iron deprivation.

In another preferred embodiment the edible composition is a nutritional composition.

Method for Preventing or Reducing the Loss of Probiotic Bacteria

The invention relates to a method for reducing or preventing the loss of probiotic bacteria during reconstitution of a composition in powder form comprising at least one probiotic bacteria and an added iron source, characterized in that an iron-milk protein complex is used as the added iron source.

The probiotic bacteria, the added iron source and the composition in powder form are as described in any embodiment of the "composition" section.

In a preferred embodiment, iron-milk protein complexes represent at least 50 wt %, more preferably at least 60 wt %, more preferably at least 70 wt %, more preferably at least 80 wt %, even more preferably at least 90 wt % of the added iron in the composition. More preferably the iron-milk protein complexes are substantially the only added iron source used in the composition. Most preferably, the iron-milk protein complexes are the only added iron source in the composition. In other words, the composition comprises no other ferrous or ferric compound added as an iron source in the composition.

The present inventors have shown that by using iron-milk protein complexes instead of other commonly added iron sources, such as ferrous sulphate heptahydrate or dissolved ferrous sulphate in spray-dried form, the loss of probiotic bacteria at the time of reconstitution of the composition could be prevented or at least significantly reduced.

The added iron source has an important impact on the survival of the probiotic bacteria, whereas the impact of iron sources present as part of an ingredient that is not intended mainly for the purpose of iron supplementation is much smaller, owing to the complexity of such ingredients. Among other reasons, the iron they contain is usually not found as free iron at the time of reconstituting the composition and thus has reduced potential harmful effects on probiotic bacteria.

The present invention will now be described in further details by the way of the following examples.

EXAMPLE 1

Effect of Iron Source on Survival of *Lactobacillus Rhamnosus*

Four powder compositions (Samples A to D) were prepared, each comprising dried *Lactobacillus rhamnosus* (deposited as CGMCC 1.3724), an iron source and 100 g of maltodextrin. The composition of the samples is summarized in Table 1 below.

TABLE 1

Composition of Samples A to D

| Ingredient | Sample A | Sample B | Sample C | Sample D |
|---|---|---|---|---|
| Dried *L. rhamnosus*[1] | 90 mg | 90 mg | 90 mg | 90 mg |
| Iron source: dissolved ferrous sulphate in spray-dried form[2] | 119 mg | 0 mg | 357 mg | 0 mg |
| Iron source: iron-casein complex[3] | 0 mg | 400 mg | 0 mg | 1200 mg |
| Maltodextrin | 100 g | 100 g | 100 g | 100 g |
| Amount of $Fe^{2+}$ provided by the iron source | 10 mg | 10 mg | 30 mg | 30 mg |

[1] Spray-dried *Lactobacillus rhamnosus* (deposited as CGMCC 1.3724) in maltodextrin matrix. The total amount of live bacteria in the composition is of 3.1E+10 CFU/g.

[2] Obtained by dissolving ferrous sulphate in water at pH2 and spray-drying in a maltodextrin matrix. This iron source contains 8.4 wt % of $Fe^{2+}$.

[3] FerriPro2, origin Riddet Institute, Massey University, New Zealand: iron-casein complex as defined as complex II in US 2015/0164123.

The Samples were produced as follows. The maltodextrin, the dried probiotic powder and the iron source were added together in a 500 mL plastic beaker and mixed for 5 minutes at 34 rpm using a Turbula® T2F dry mixer (WAB, Switzerland). An amount of 25 g of freshly mixed sample was diluted 1/10 in an aqueous tryptone salt solution supplemented with anti-foaming agent at 37° C. After 5 minutes of homogenization using a Masticator® (IUL, Spain), decimal dilutions were performed. The appropriate dilution resulting in 30-300 colonies after incubation was then transferred to a petri dish and mixed with MRS agar according to the pour plate method. Once solidified the plates were incubated at 37° C. under aerobic conditions. After 48 h of incubation the colonies present on the plates were counted.

Figure 1:
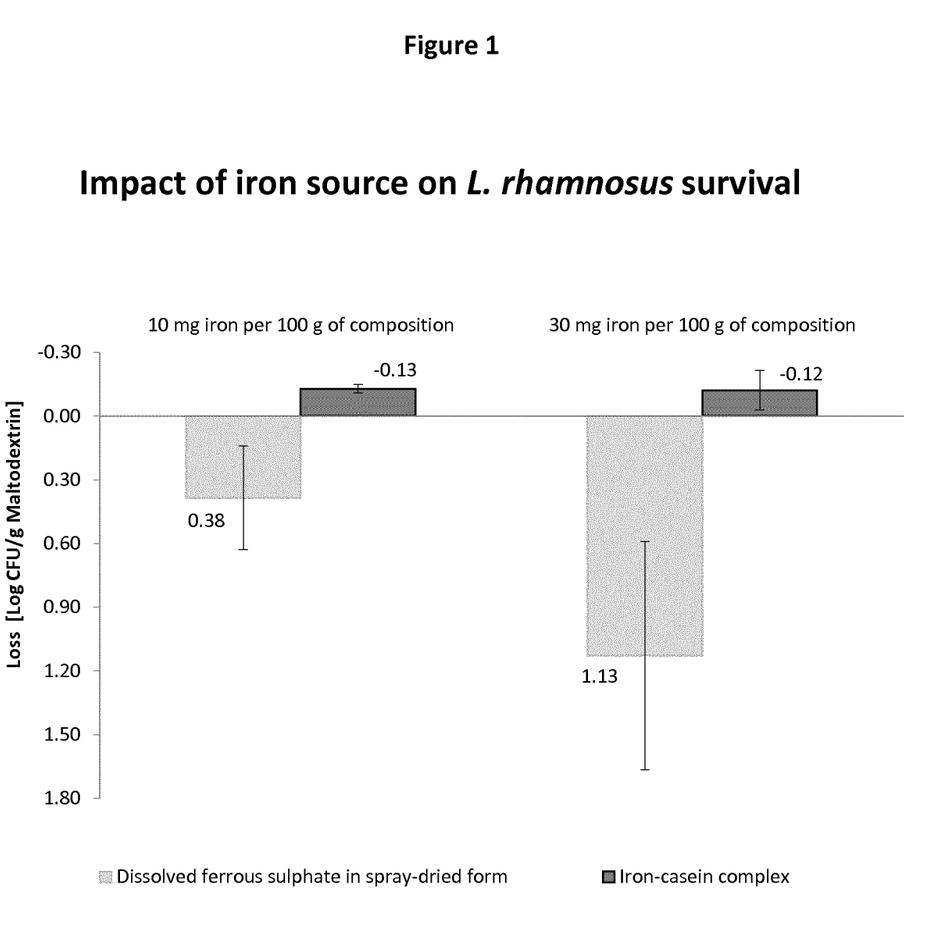
FIG. 1: Graphic representation of the loss of viability of *Lactobacillus rhamnosus* (deposited as CGMCC 1.3724) in compositions having respectively 10 and 30 mg of iron per 100 g of composition. Two different iron sources are compared: dissolved ferrous sulphate in spray-dried form and an iron-casein complex. The loss of viable *Lactobacillus rhamnosus* is significantly lower with the iron-casein complex, at both iron concentrations.

The results are summarized in FIG. 1. It is clear from this graph that significant loss of live *L. rhamnosus* was observed in the reconstituted compositions when dissolved ferrous sulphate in spray-dried form was used. In contrast, when the iron-casein complex was used in the same conditions, with the same amount of *L. rhamnosus* and same amount of iron, no significant loss of *L. rhamnosus* was observed.

EXAMPLE 2

Effect of Iron Source on Survival of *Bifidobacterium Longum*

Five powder compositions (Samples E to I) were prepared, each comprising dried *Bifidobacterium longum* (deposited as ATCC BAA-999) an iron source and 100 g of maltodextrin. The composition of the five samples is summarized in Table 2 below.

TABLE 2

Composition of Samples E to I

| Ingredient | Sample E | Sample F | Sample G | Sample H | Sample I |
| --- | --- | --- | --- | --- | --- |
| Dried *B. longum*[1] | 100 mg | 100 mg | 100 mg | 100 mg | 100 mg |
| Iron source: dissolved ferrous sulphate in spray-dried form[2] | 0 mg | 298 mg | 0 mg | 595 mg | 0 mg |
| Iron source: iron-casein complex[3] | 0 mg | 0 mg | 1000 mg | 0 mg | 2000 mg |
| Maltodextrin | 100 g | 100 g | 100 g | 100 g | 100 g |
| Amount of $Fe^{2+}$ provided by the iron source | 0 mg | 25 mg | 25 mg | 50 mg | 50 mg |

[1] Spray-dried *Bifidobacterium longum* (deposited as ATCC BAA-999) in maltodextrin matrix. The total amount of live bacteria in the composition is of 2.4E+10 CFU/g.
[2] Obtained by dissolving ferrous sulphate in water at pH 2 and spray-drying in a maltodextrin matrix. This iron source contains 8.4 wt % of $Fe^{2+}$.
[3] Ferripro2, origin Riddet Institute, Massey University, New Zealand The Samples were produced as follows. The maltodextrin, the dried probiotic powder and the iron source were added together in a 500 mL plastic beaker and mixed for 5 minutes at 34 rpm using a Turbula® T2F dry mixer (WAB, Switzerland). An amount of 25 g of freshly mixed sample was diluted 1/10 in an aqueous tryptone salt solution supplemented with anti-foaming agent at 37° C. After 5 minutes of homogenization using a Masticator® (IUL, Spain), decimal dilutions were performed. The appropriate dilution resulting in 30-300 colonies after incubation was then transferred to a petri dish and mixed with RCA agar according to the pour plate method. Once solidified the plates were incubated at 37° C. under anaerobic conditions. After 48 h of incubation the colonies present on the plates were counted.

Figure 2:
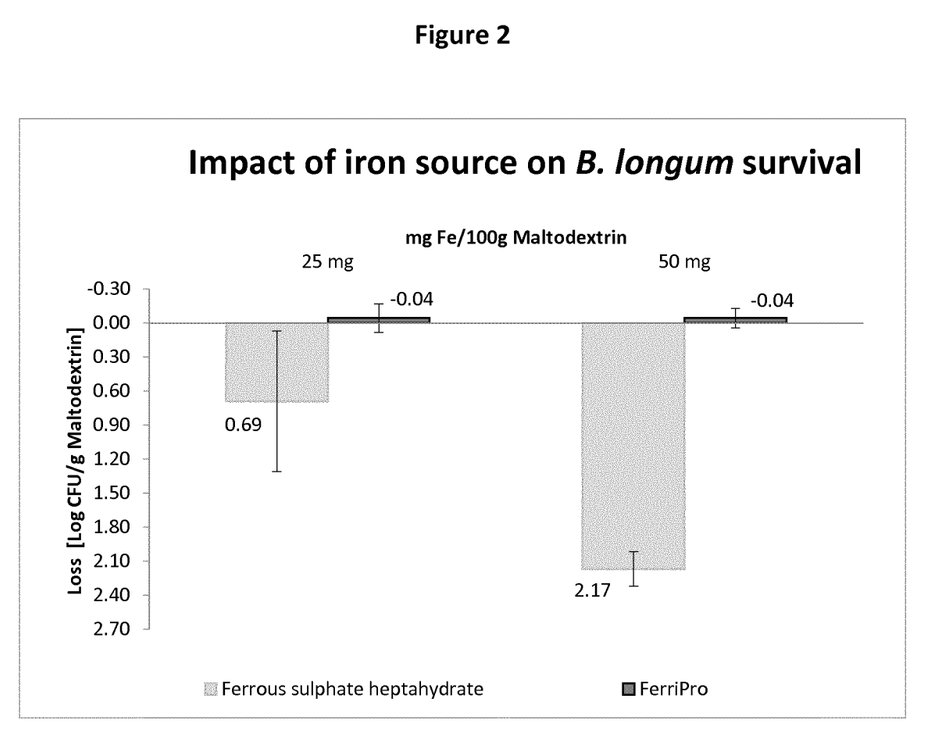
FIGS. 2-6 are graphs respectively summarizing the results from Example 2-6 herein.

The results are summarized in the graph of FIG. 2. It is clear from this graph that significant loss of live *B. longum* was observed in the reconstituted compositions when dissolved ferrous sulphate in spray-dried form was used. In contrast, when the iron-casein complex was used in the same conditions, with the same amount of *B. longum* and same amount of iron, no significant loss of *B. longum* was observed.

EXAMPLE 3

Effect of Iron Source on Survival of *Bifidobacterium Longum*

Five powder compositions (Samples I to M) were prepared, each comprising dried *Bifidobacterium longum* (deposited as ATCC BAA-999) an iron source and 100 g of infant formula. The composition of the five samples is summarized in Table 3 below.

The Samples were produced as follows. The infant formula, the dried probiotic powder and the iron source were added together in a 500 mL plastic beaker and mixed for 5 minutes at 34 rpm using a Turbula® T2F dry mixer (WAB, Switzerland). An amount of 25 g of freshly mixed sample was diluted 1/10 in an aqueous tryptone salt solution supplemented with anti-foaming agent at 37° C. After 5 minutes of homogenization using a Masticator® (IUL, Spain), decimal dilutions were performed. The appropriate dilution resulting in 30-300 colonies after incubation was then transferred to a petri dish and mixed with RCA agar according to the pour plate method. Once solidified the plates were incubated at 37° C. under anaerobic conditions. After 48 h of incubation the colonies present on the plates were counted.

Figure 3:
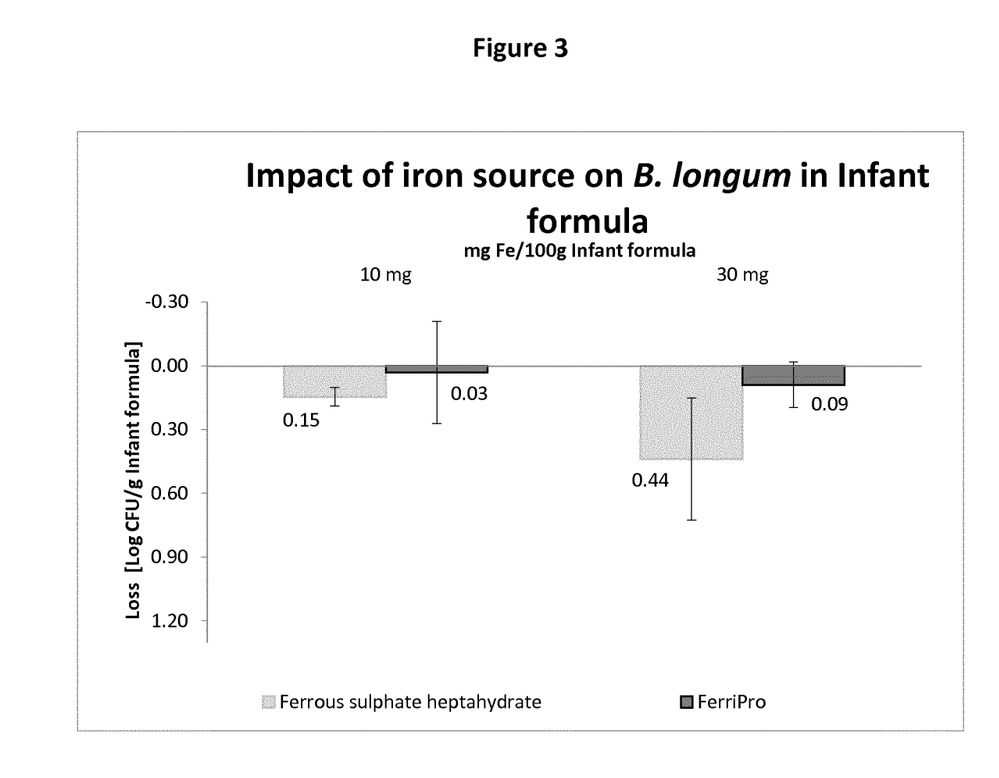

The results are summarized in the graph of FIG. 3. It is clear from this graph that the loss of live *B. longum* in the reconstituted compositions was significantly smaller when the iron source used was iron-casein complex than when dissolved ferrous sulphate in spray-dried form was used in the same conditions and with the same amount of *B. longum* and same amount of iron.

EXAMPLE 4

Effect of Iron Source on Survival of *Lactobacillus Paracasei*

Five powder compositions (Samples N to R) were prepared, each comprising dried *Lactobacillus paracasei* (deposited as CNCM 1-2116), an iron source and 100 g of maltodextrin. The composition of the five samples is summarized in Table 4 below.

TABLE 3

Composition of Samples I to M

| Ingredient | Sample I | Sample J | Sample K | Sample L | Sample M |
| --- | --- | --- | --- | --- | --- |
| Dried *B. longum*[1] | 90 mg | 90 mg | 90 mg | 90 mg | 90 mg |
| Iron source: dissolved ferrous sulphate in spray-dried form[2] | 0 mg | 119 mg | 0 mg | 357 mg | 0 mg |
| Iron source: iron-casein complex[3] | 0 mg | 0 mg | 478 mg | 0 mg | 1439 mg |
| Infant formula | 100 g | 100 g | 100 g | 100 g | 100 g |
| Amount of $Fe^{2+}$ provided by the iron source | 0 mg | 10 mg | 10 mg | 30 mg | 30 mg |

[1] Spray-dried *Bifidobacterium longum* (deposited as ATCC BAA-999) in maltodextrin matrix. The total amount of live bacteria in the composition is of 2.4E+10 CFU/g.
[2] Obtained by dissolving ferrous sulphate in water at pH 2 and spray-drying in a maltodextrin matrix. This iron source contains 8.4 wt % of $Fe^{2+}$.
[3] Ferripro2, origin Riddet Institute, Massey University, New Zealand

TABLE 4

Composition of Samples N to R

| Ingredient | Sample N | Sample O | Sample P | Sample Q | Sample R |
|---|---|---|---|---|---|
| Dried *L. paracasei*[1] | 100 mg | 100 mg | 100 mg | 100 mg | 100 mg |
| Iron source: dissolved ferrous sulphate in spray-dried form[2] | 0 mg | 298 mg | 0 mg | 595 mg | 0 mg |
| Iron source: iron-casein complex[3] | 0 mg | 0 mg | 1196 mg | 0 mg | 2392 mg |
| Maltodextrin | 100 g | 100 g | 100 g | 100 g | 100 g |
| Amount of $Fe^{2+}$ provided by the iron source | 0 mg | 25 mg | 25 mg | 50 mg | 50 mg |

[1] Spray-dried *Lactobacillus paracasei* (deposited as CNCM I-2116) in maltodextrin matrix. The total amount of live bacteria in the composition is of 2.4E+10 CFU/g.
[2] Obtained by dissolving ferrous sulphate in water at pH 2 and spray-drying in a maltodextrin matrix. This iron source contains 8.4 wt % of $Fe^{2+}$.
[3] Ferripro2, origin Riddet Institute, Massey University, New Zealand The Samples were produced as follows. The maltodextrin, the dried probiotic powder and the iron source were added together in a 500 mL plastic beaker and mixed for 5 minutes at 34 rpm using a Turbula® T2F dry mixer (WAB, Switzerland). An amount of 25 g of freshly mixed sample was diluted 1/10 in an aqueous tryptone salt solution supplemented with anti-foaming agent at 37° C. After 5 minutes of homogenization using a Masticator® (IUL, Spain), decimal dilutions were performed. The appropriate dilution resulting in 30-300 colonies after incubation was then transferred to a petri dish and mixed with MRS agar according to the pour plate method. Once solidified the plates were incubated at 37° C. under aerobic conditions. After 48 h of incubation the colonies present on the plates were counted.

Figure 4:
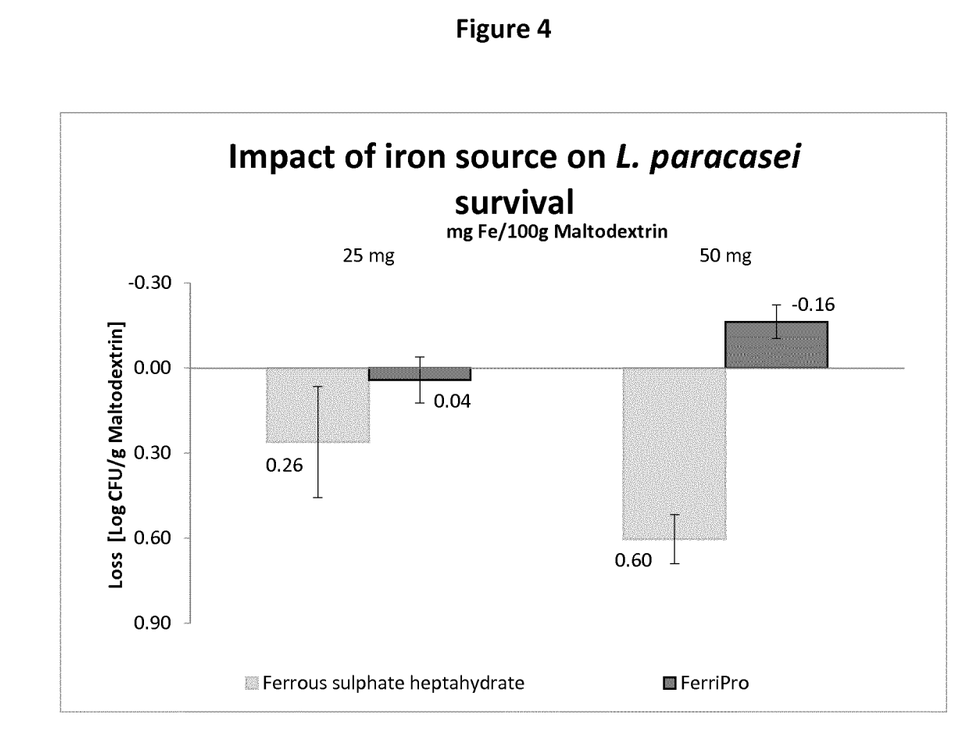

The results are summarized in the graph of FIG. 4. It is clear from this graph that significant loss of live *L. paracasei* was observed in the reconstituted compositions when dissolved ferrous sulphate in spray-dried form was used. In contrast, when the iron-casein complex was used in the same conditions, with the same amount of *L. paracasei* and same amount of iron, no significant loss of *L. paracasei* was observed.

EXAMPLE 5

Effect of Iron Source on Survival of *Lactobacillus Paracasei*

Five powder compositions (Samples S to W) were prepared, each comprising dried *Lactobacillus paracasei* (deposited as CNCM 1-2116), an iron source and 100 g of infant formula. The composition of the five samples is summarized in Table 5 below.

The Samples were produced as follows. The infant formula, the dried probiotic powder and the iron source were added together in a 500 mL plastic beaker and mixed for 5 minutes at 34 rpm using a Turbula® T2F dry mixer (WAB, Switzerland). An amount of 25 g of freshly mixed sample was diluted 1/10 in an aqueous tryptone salt solution supplemented with anti-foaming agent at 37° C. After 5 minutes of homogenization using a Masticator® (IUL, Spain), decimal dilutions were performed. The appropriate dilution resulting in 30-300 colonies after incubation was then transferred to a petri dish and mixed with MRS agar according to the pour plate method. Once solidified the plates were incubated at 37° C. under aerobic conditions. After 48 h of incubation the colonies present on the plates were counted.

Figure 5:
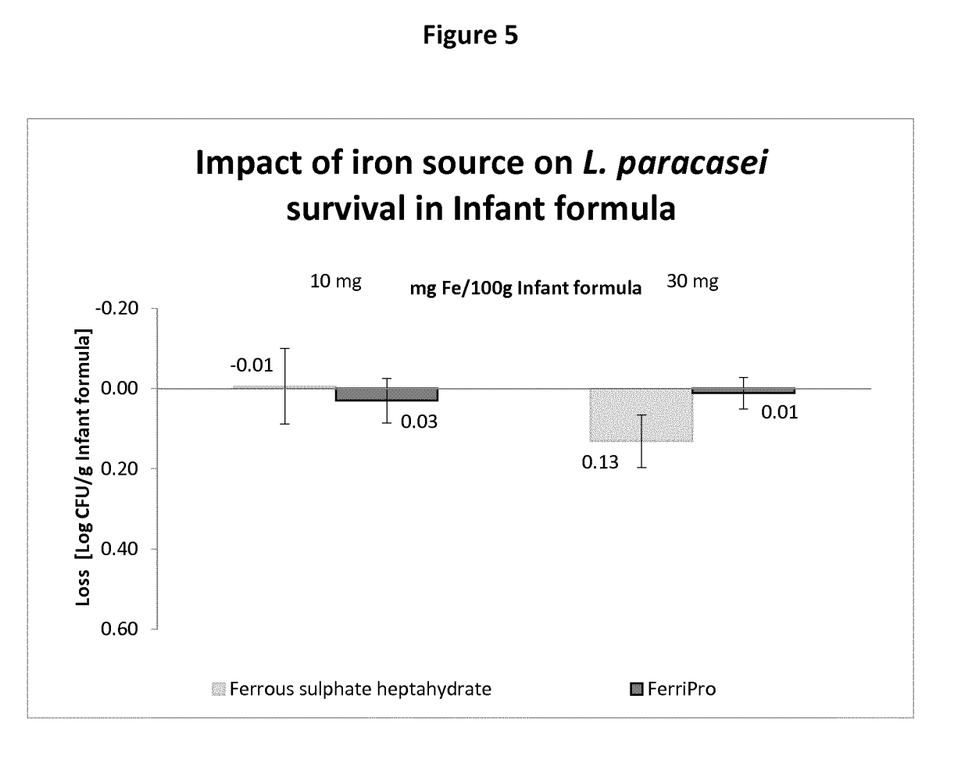

The results are summarized in the graph of FIG. 5. Although no significant loss of probiotic was observed when each of the iron source was added in an amount such as to provide 10 mg of iron, a clear impact on the viability of *L. paracasei* was observed in the reconstituted compositions when dissolved ferrous sulphate in spray-dried form was used in an amount providing 30 mg of iron. In contrast, when the iron-casein complex was used in the same conditions, with the same amount of *L. paracasei* and same amount of iron, no significant loss of *L. paracasei* was observed.

EXAMPLE 6

Effect of Iron Source on Survival of *Lactobacillus Rhamnosus*

Five powder compositions (Samples X to BB) were prepared, each comprising dried *Lactobacillus rhamnosus* (deposited as CGMCC 1.3724), an iron source and 100 g of infant formula. The composition of the five samples is summarized in Table 6 below.

TABLE 5

Composition of Samples S to W

| Ingredient | Sample S | Sample T | Sample U | Sample V | Sample W |
|---|---|---|---|---|---|
| Dried *L. paracasei*[1] | 90 mg | 90 mg | 90 mg | 90 mg | 90 mg |
| Iron source: dissolved ferrous sulphate in spray-dried form[2] | 0 mg | 119 mg | 0 mg | 357 mg | 0 mg |
| Iron source: iron-casein complex[3] | 0 mg | 0 mg | 478 mg | 0 mg | 1435 mg |
| Infant formula | 100 g | 100 g | 100 g | 100 g | 100 g |
| Amount of $Fe^{2+}$ provided by the iron source | 0 mg | 10 mg | 10 mg | 30 mg | 30 mg |

[1] Spray-dried *Lactobacillus paracasei* (deposited as CNCM I-2116) in maltodextrin matrix. The total amount of live bacteria in the composition is of 2.4E+10 CFU/g.
[2] Obtained by dissolving ferrous sulphate in water at pH 2 and spray-drying in a maltodextrin matrix. This iron source contains 8.4 wt % of $Fe^{2+}$.
[3] Ferripro2, origin Riddet Institute, Massey University, New Zealand

TABLE 6

Composition of Samples X to BB

| Ingredient | Sample X | Sample Y | Sample Z | Sample AA | Sample BB |
|---|---|---|---|---|---|
| Dried *L. rhamnosus*[1] | 90 mg | 90 mg | 90 mg | 90 mg | 90 mg |
| Iron source: dissolved ferrous sulphate in spray-dried form[2] | 0 mg | 119 mg | 0 mg | 357 mg | 0 mg |
| Iron source: iron-casein complex[3] | 0 mg | 0 mg | 478 mg | 0 mg | 1435 mg |
| Infant formula | 100 g | 100 g | 100 g | 100 g | 100 g |
| Amount of $Fe^{2+}$ provided by the iron source | 0 mg | 10 mg | 10 mg | 30 mg | 30 mg |

[1]*Lactobacillus rhamnosus* (deposited as CGMCC 1.3724) in an amount of 3.1E+10 CFU/g, in maltodextrin.
[2]Obtained by dissolving ferrous sulphate in water at pH 2 and spray-drying in a maltodextrin matrix. This iron source contains 8.4 wt % of $Fe^{2+}$.
[3]Ferripro2, origin Riddet Institute, Massey University, New Zealand The Samples were produced as follows. The infant formula, the dried probiotic powder and the iron source were added together in a 500 mL plastic beaker and mixed for 5 minutes at 34 rpm using a Turbula® T2F dry mixer (WAB, Switzerland). An amount of 25 g of freshly mixed sample was diluted 1/10 in an aqueous tryptone salt solution supplemented with anti-foaming agent at 37° C. After 5 minutes of homogenization using a Masticator® (IUL, Spain), decimal dilutions were performed. The appropriate dilution resulting in 30-300 colonies after incubation was then transferred to a petri dish and mixed with MRS agar according to the pour plate method. Once solidified the plates were incubated at 37° C. under aerobic conditions. After 48 h of incubation the colonies present on the plates were counted.

Figure 6:
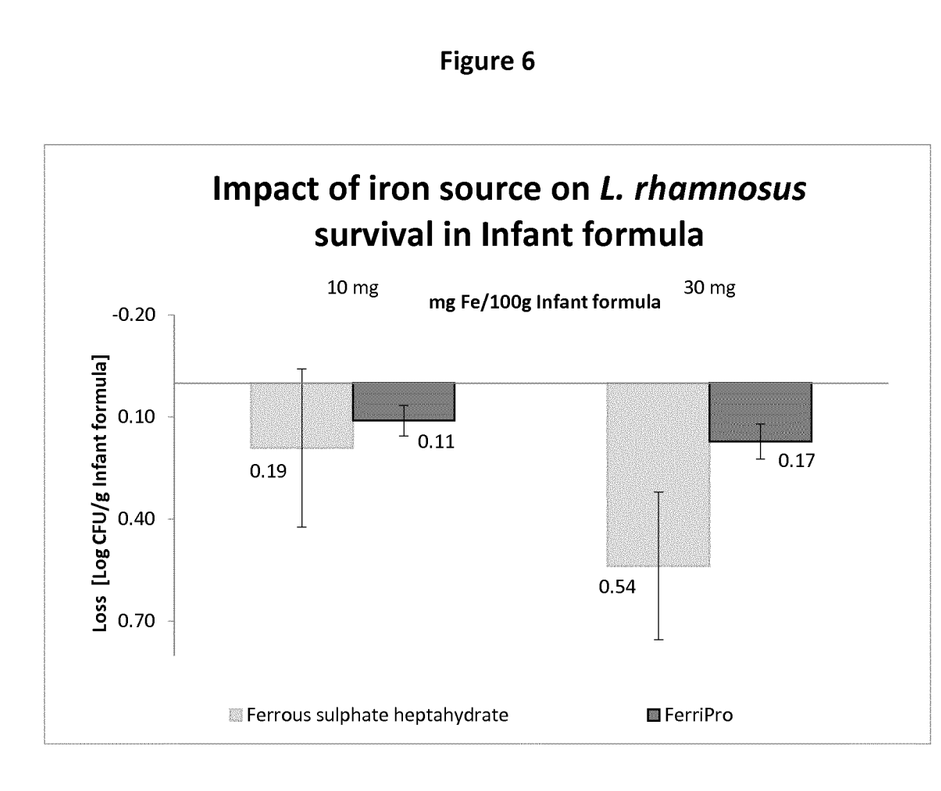

The results are summarized in the graph of FIG. 6. It is clear from this graph that significant loss of live *L. rhamnosus* was observed in the reconstituted compositions when dissolved ferrous sulphate in spray-dried form was used. In contrast, when the iron-casein complex was used in the same conditions, with the same amount of *L. rhamnosus* and same amount of iron, the loss of *L. rhamnosus* was significantly reduced.

The invention claimed is:

1. A composition in powder form, the composition comprising at least one probiotic bacteria and further comprising an iron-milk protein complex in which the milk protein is selected from the group consisting of casein, a casein derivative, a fraction of casein, and a mixture thereof.

2. The composition according to claim 1, wherein the iron-milk protein complex comprises exogenous iron.

3. The composition according to claim 1, wherein the iron-milk protein complex comprises exogenous phosphorus.

4. The composition according to claim 1, wherein the iron in the iron-milk protein complex is $Fe^{3+}$.

5. The composition according to claim 1, wherein the composition in powder form is a nutritional composition.

6. The composition according to claim 1, wherein the iron-milk protein complex is present in an amount comprising 1 to 300 mg of the iron per 100 g of the composition.

7. The composition according to claim 1, wherein the milk protein in the iron-milk protein complex consists of casein.

8. The composition according to claim 1, wherein the milk protein in the iron-milk protein complex is casein, and the iron-milk protein complex consists of the casein and the iron.

9. The composition according to claim 2, wherein a weight ratio of the milk protein to the exogenous iron is between 50:1 and 19.5:1.

10. The composition according to claim 3, wherein the exogenous phosphorus comprises orthophosphorus, and a weight ratio of the milk protein to the orthophosphorus is 20:1 to 8:1.

11. The composition according to claim 3, wherein the iron-milk protein complex consists of the iron, the milk protein and the exogenous phosphorus.

12. The composition according to claim 1, wherein the iron-milk protein complex comprises the only iron in the composition.

13. The composition according to claim 1, further comprising polyphenols.

* * * * *